United States Patent [19]

Kraska et al.

[11] Patent Number: 4,678,868
[45] Date of Patent: Jul. 7, 1987

[54] HERMETIC ELECTRICAL FEEDTHROUGH ASSEMBLY

[75] Inventors: Robert E. Kraska, Minneapolis; Frank J. Wilary, Plymouth; Joseph F. Lessar, Coon Rapids, all of Minn.

[73] Assignee: Medtronic, Inc., Minneapolis, Minn.

[21] Appl. No.: 635,576

[22] Filed: Jul. 30, 1984

Related U.S. Application Data

[63] Continuation-in-part of Ser. No. 51,987, Jun. 25, 1979, abandoned, which is a continuation-in-part of Ser. No. 7,153, Jan. 29, 1979, abandoned.

[51] Int. Cl.⁴ .................... H01B 17/30; C03C 27/04
[52] U.S. Cl. .......................... 174/152 GM; 228/122
[58] Field of Search .................. 174/50.61, 152 GM; 228/122, 124

[56] References Cited

U.S. PATENT DOCUMENTS

| 3,273,979 | 9/1966 | Budnick | 228/122 X |
| 3,370,874 | 2/1968 | Scherer et al. | 174/50.61 X |
| 3,873,944 | 3/1975 | Vaguine et al. | 228/124 X |
| 3,906,311 | 9/1975 | Shoot et al. | 174/50.61 X |
| 3,920,888 | 11/1975 | Barr | 174/152 GM |
| 4,180,700 | 12/1979 | Kraska et al. | 174/152 GM |

FOREIGN PATENT DOCUMENTS 8001620 8/1980 PCT Int'l Appl. ......... 174/152 GM

Primary Examiner—Laramie E. Askin
Attorney, Agent, or Firm—Vidas & Arrett

[57] ABSTRACT

A hermetic feedthrough consisting of a niobium electrical lead-in wire surrounded by an alumina insulator which is carried by a niobium ferrule, the feedthrough being particularly adapted for being welded to the titanium container of an implantable medical device. The niobium and alumina parts are joined together by means of a pure gold braze, the surfaces of the alumina being first metallized with a layer of niobium, titanium or niobium/titanium and an optional overlying layer of gold.

5 Claims, 1 Drawing Figure

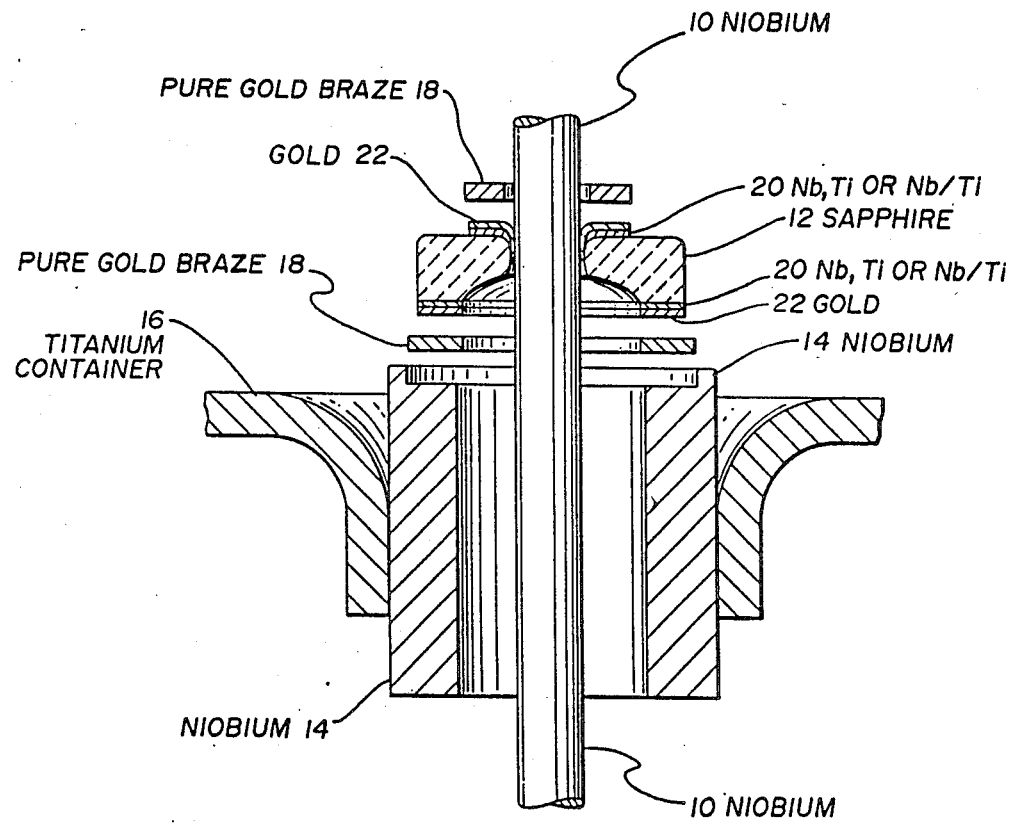

HERMETIC ELECTRICAL FEEDTHROUGH ASSEMBLY

CROSS-REFERENCE TO RELATED APPLICATIONS

This application is a continuation-in-part of application Ser. No. 51,987, filed June 25, 1979 (now abandoned) which in turn is a continuation-in-part of application Ser. No. 7,153, filed Jan. 29, 1979 (now abandoned).

SUMMARY OF THE INVENTION

This invention relates to a hermetic electrical feedthrough assembly specifically designed for being welded to the titantium container of an implantable medical device, such as a heart pacemaker or the like, to provide a hermetically sealed electrical inlet to the device. The feedthrough makes use of a niobium pin and ferrule and an alumina ($Al_2O_3$), particularly sapphire, insulator.

The optical transparency of the sapphire form of alumina allows visual inspection of the sapphire-to-niobium bond for the presence of defects. Sapphire is an aluminum oxide which is grwon with a single crystal lattice structure and can be easily cut and polished to optical clarity without creating cracks or defects. If cracks or defects do result during preparation of a sapphire insulator for a feedthrough or during fabrication of the feedthrough assembly, they can be easily seen at low magnification. The ease of visual inspection consequently allows for 100% final product inspection. Thus, even though ordinary polycrystalline alumina can be used in this invention, the single crystal form of alumina known as sapphire is especially preferred.

The specific combination of materials, i.e., sapphire and niobium, is resistant to defect formation during manufacture. Hence, greater yields are provided. Off-the-shelf watch jewels of sapphire are readily available for use in accordance with this invention.

Hermetic seals in electrical feedthroughs consisting of the specific combinations of materials disclosed herein and prepared according to this invention have been found to be excellent in resisting delamination between the insulator and metal members of the feedthrough, i.e., they are highly resistant to stress-induced cracking during fabrication or testing.

More importantly, the feedthroughs of the invention can be used as a substitute for feedthroughs having a titanium ferrule. Although titanium ferrules are readily welded to titanium containers and would, therefore, be the preferred choice for feedthrough ferrules in titanium containers, titanium ferrules are not compatible with alumina insulators from the brazing standpoint.

Specifically, with respect to hermetically sealed titanium containers required for implantable medical devices and in which the only satisfactory brazing material is gold or gold alloys due to their corrosion resistance but which have high brazing temperature on the order of 1985°–2000° F., titanium undergoes an alpha-beta transition during such high temperature brazing resulting in uncontrollable dimensional changes in the feedthrough pieceparts, making it impossible for them to remain within dimensional specifications and causing fractures in the alumina.

Consequently, titanium ferrules cannot be used. Much effort has been extended in the art in attempting to adapt titanium to use with alumina insulators in feedthroughs. The results have not been satisfactory in providing feedthroughs having titanium ferrules and alumina insulators.

Ordinarily, it has not been expected that niobium can be welded to titanium, there being such a melting point differential between the two metals i.e., about 700° C. Therefore, the art has not considered the use of a niobium ferrule under these circumstances. However, niobium is body compatible and corrosion resistant and does not undergo the alph-beta phase transformation which titanium undergoes. Contrary to the accepted position in the art concerning the apparent inability of niobium to be welded to titanium for effecting a hermetic seal, it has been found in making this invention that niobium is laser weldable to titanium thereby making niobium/alumina feedthroughs appropriate for use in titanium containers.

It is a purpose of this invention to provide in one preferred embodiment high yield electrical feedthroughs which can be optically inspected.

Additionally, and more importantly, it is a general purpose of this invention to provide improved hermetic electrical feedthroughs which are particularly adapted for welding to encapsulated electrical devices having titanium containers, such as electrochemical cells, heartpacers and the like for human implant. Such devices require high assurety against the presence of defects and loss of hermeticity in the feedthroughs. This is provided by this invention as well as other advantages which will become apparent hereinbelow.

The improved feedthrough of the invention consists of a niobium lead wire extending through an alumina insulator, preferably disc-like in shape. The alumina insulator is carried by a niobium ferrule or the like. The assembly is brazed together by means of a gold braze, the braze material being provided as a preform. The surfaces of the alumina in the brazed areas are first metallized with a discrete layer of niobium, titanium or a composition of the two, i.e., niobium/titanium, and an optional layer of gold may be included overlying the niobium/titanium. Niobium is preferred over the titanium or the niobium/titanium alloys.

BRIEF DESCRIPTION OF THE DRAWING

The FIGURE is a schematic cross-section of a feedthrough combined with a titanium container according to the invention with the piece parts thereof shown in exploded view.

DETAILED DESCRIPTION OF THE INVENTION

Referring to the FIGURE, all the embodiments of the invention include a more or less centrally positioned niobium lead-in wire or pin 10 extending through an alumina, preferably sapphire, insulator body 12. Body 12 is ordinarily generally disc shaped but may be shaped otherwise. The feedthrough assembly also includes a niobium ferrule or the like 14 which may more or less peripherally contact sapphire body 12 as is well known in the case of metal ferrule and glass insulator arrangements already known in this art. Ferrule 14 is utilized for supporting the insulator and pin and for mounting the feedthrough in the container. This feedthrough is mounted in a titanium encapsulating structure or container 16 shown only in fragment, which contains an electrical device (not shown) for human implant. The ferrule is welded to the titanium container utilizing standard laser welding techniques thereby hermetically sealing the feedthrough and container together.

The niobium used for the lead wire and ferrule herein is preferably pure niobium or what is commonly sold as being substantially pure. It may also be a niobium alloy so long as its thermal expansion coefficient remains about ±10% of that of commercially pure niobium. An example of such an alloy is 99Nb-1Zr (Wt. %). Other alloys such as 44-56% niobium, balance titanium are also acceptable. Herein, when these components are described as consisting essentially of niobium, such alloys are intended to be included along with substantially pure niobium.

The members of the feedthrough are assembled together by brazing. As is common practice in the art, brazing of the feedthrough assembly may be accomplished by placing preform rings 18 of the brazing material at the joints to be brazed and heating the assembly to the appropriate melting temperature of the braze material.

The braze material is gold i.e., commercially pure gold (99.9%).

The use of pure gold braze material requires that the sapphire or alumina insulator must first be provided with a metallization coating 20 of niobium, titanium or niobium/titanium.

A coating 22 of gold over the niobium or titanium in the areas where the brazed joint is to be formed may be optionally included.

Various proportions of nibium and titanium may be co-sputtered to form a metallization layer 20 of niobium/titanium. Such an alloy is referred to herein as "niobium/titanium". All of these coatings are preferably formed by sputtering and should be very thin. Preferably, the niobium, titanium or niobium/titanium coating will have a thickness on the order of about 10,000 angstroms and the optional gold layer will have a thickness on the order of about 2,000 angstroms.

In the instance of a metallization layer of niobium, it is critical that the layer be between about 2,000 angstroms and about 40,000 angstroms in thickness. Any thicker layer cause bubbles and voids to form resulting in weakness; any thinner and the layer is completely dissolved by the gold.

In the instance of a metallization layer of titanium, it is critical that the layer be between about 5,000 angstroms and about 40,000 angstroms (10,000-30,000 angstroms, preferred) in thickness. Any thicker layer causes the alumina insulator to crack; any thinner and the titanium is completely dissolved by the gold.

In the instance of a metallization layer of an alloy of niobium/titanium the thickness range of the layer appears to be similar to that for niobium alone.

A metallized version including all optional variations is shown for exemplification in the FIGURE, the niobium, titanium or niobium/titanium and gold layers being schematically indicated at 20 and 22, respectively. The gold braze material is provided in the form of a gold preform 18. Niobium is the preferred coating material 20 although titanium is equally acceptable for use in dry and low temperature environments. Niobium is less susceptible to degradation and corrosion when exposed to moisture than the titanium or niobium/titanium is.

Any of the variations described above and any combinations thereof may be used in any feedthrough configuration.

The sapphire used herein may be the "clear" sapphire or the "doped" sapphire i.e., sapphire containing a few tenths of a percent of a dopant such as chromium, cobalt or nickel and taking on a characteristic color such as ruby, blue or emerald, respectively.

Having described the invention, the exclusive rights and privileges thereto are to be defined by the following claims in the light of the foregoing description.

We claim:

1. An electrical feedthrough comprising an electrical lead-wire consisting essentially of niobium; an alumina insulator around a portion of the lead-wire; a ferrule consisting essentially of niobium positioned around at least a portion of the alumina insulator for receiving same, and brazes joining the lead-wire to the insulator and the insulator to the ferrule, the brazes consisting essentially of substantially pure gold, the alumina insulator being first metallized with a metal selected from the group consisting of niobium, titanium and niobium/titanium at the brazed areas and wherein the metallizations have a thickness of from about 2,000 to about 40,000 angstroms when they are niobium, from about 5,000 to about 40,000 angstroms when they are titanium and from about 2,000 to about 40,000 angstroms when they are niobium/titanium.

2. The feedthrough of claim 1 in which the metallizations of the alumina insulator are coated with a gold layer.

3. The feedthrough of claim 2 in which each metallization is about 10,000 angstroms thick and the gold layer is less thick.

4. The feedthrough of claim 3 in which each gold layer is about 2,000 angstroms thick.

5. The feedthrough according to claim 1 in which the alumina is sapphire.

* * * * *

UNITED STATES PATENT AND TRADEMARK OFFICE
CERTIFICATE OF CORRECTION

PATENT NO. : 4,678,868
DATED : July 7, 1987
INVENTOR(S) : Robert E. Kraska et al It is certified that error appears in the above-identified patent and that said Letters Patent is hereby corrected as shown below:

Column 1, line 25 "grwon" should be --grown--.

Column 1, line 59 "temperature" should be --temperatures--.

Column 4, line 46 "the" should be --each--.

Signed and Sealed this

Twenty-fourth Day of November, 1987

Attest:

DONALD J. QUIGG

*Attesting Officer*  *Commissioner of Patents and Trademarks*